United States Patent [19]

Walker

[11] 4,130,016

[45] Dec. 19, 1978

[54] ADIABATIC CALORIMETER APPARATUS AND METHOD FOR MEASURING THE ENERGY CHANGE IN A CHEMICAL REACTION

[75] Inventor: Lynn C. Walker, Midland, Mich.

[73] Assignee: The Dow Chemical Company, Midland, Mich.

[21] Appl. No.: 822,595

[22] Filed: Aug. 8, 1977

[51] Int. Cl.² .............................................. G01K 17/00
[52] U.S. Cl. ................................. 73/190 R; 23/230 R; 422/51
[58] Field of Search ................... 73/190 R; 23/230 R, 23/253 R

[56] References Cited

U.S. PATENT DOCUMENTS

| 1,247,998 | 11/1917 | Parr .................................. 73/191 |
| 3,365,944 | 1/1968 | Hoagland et al. ..................... 73/190 |
| 3,667,294 | 6/1972 | Schoenlaub ........................ 73/190 |

*Primary Examiner*—Herbert Goldstein

*Attorney, Agent, or Firm*—V. Dean Clausen

[57] ABSTRACT

The adiabatic calorimeter apparatus disclosed herein is designed for chemical hazard research, particularly the study of self-heating reactions, which can result in a runaway situation. The reaction vessel and associated components in this apparatus closely simulate the structure and operation of a typical chemical plant reactor. The reaction vessel is fitted into a metal shell and the entire unit is suspended in an insulated oven. During the exothermic reaction the adiabatic temperature rise and pressure rise is simultaneously monitored and recorded as a function of time. A first stage control system maintains the temperature of the reaction vessel in equilibrium with the reaction mix and utilizes electrical energy to compensate out the heat capacity effect of the reactor. A second stage control keeps the temperature of the oven and the reaction vessel at the same level, to insure that the reaction is taking place in an adiabatic environment.

16 Claims, 1 Drawing Figure

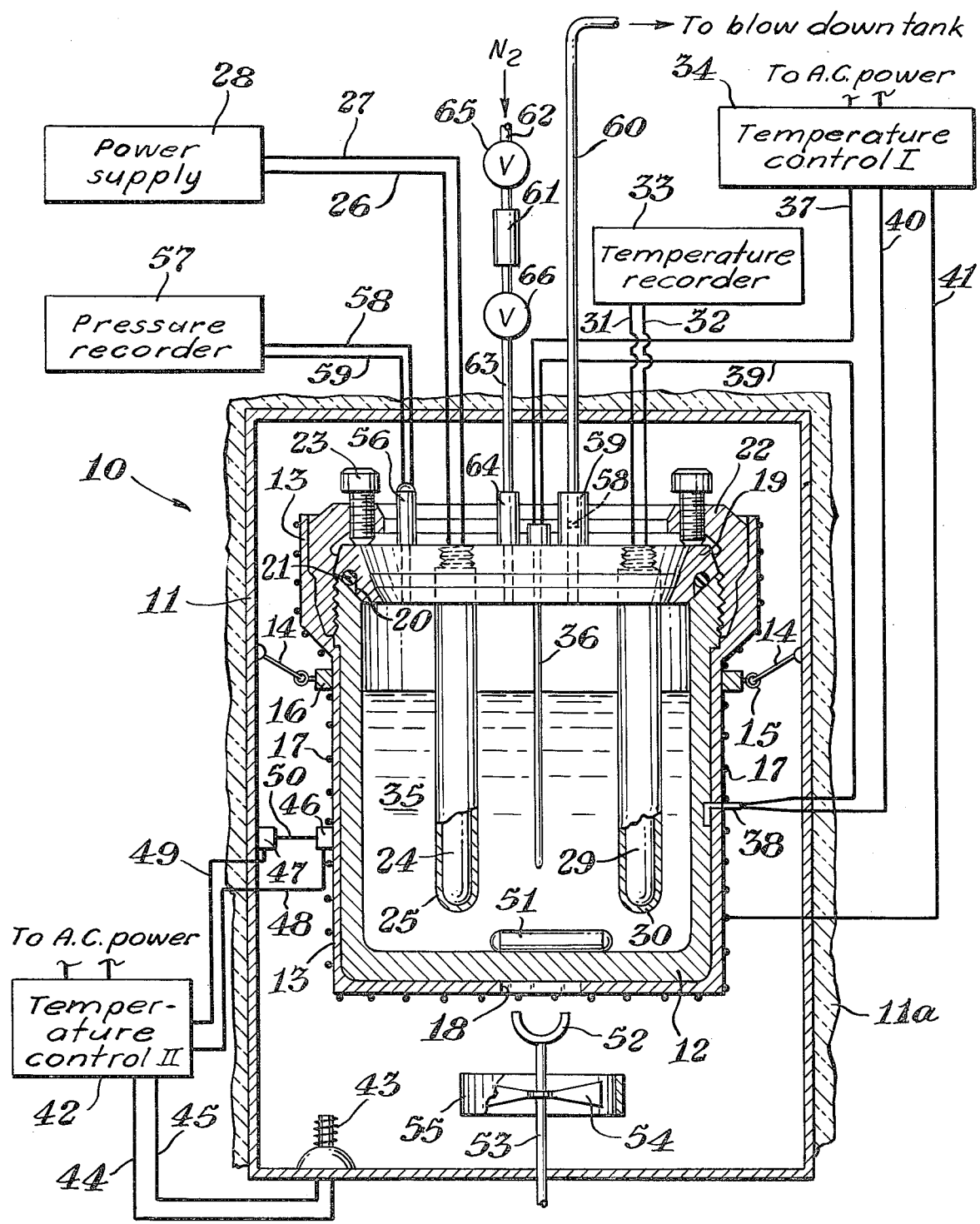

ADIABATIC CALORIMETER APPARATUS AND METHOD FOR MEASURING THE ENERGY CHANGE IN A CHEMICAL REACTION

BACKGROUND OF THE INVENTION

Broadly, the invention relates to a system and method for measuring energy changes in exothermic chemical reactions. More particularly, the invention is directed to a calorimeter apparatus capable of measuring the adiabatic temperature rise, and pressure change, as a function of time, which occurs in a self-heating reaction.

In the commercial production of chemical compounds, the mass of the reactant materials, in relation to the mass of the reactor vessel, is usually a large ratio, such as 10:1. In addition, the total heat capacity of the reactants, as compared to the heat capacity of the reactor, is an even larger ratio. If loss of cooling occurs during the reaction, the reactor usually does not provide an adequate heat sink for absorbing the heat energy liberated by the reaction. In this situation the liberated heat causes the temperature of the reactant mass to rise sharply, and the reaction proceeds at a much faster rate.

When the reaction mass begins to generate more heat than the system can remove, it becomes a self-heating reaction, with corresponding high temperatures and pressures. If cooling cannot be restored, or the frangible relief systems on the reactor cannot relieve the overpressure condition, the reaction becomes a runaway. In a runaway situation the reactor usually fails.

Because of the situation described above there is a need for a laboratory instrument in which a runaway reaction can be simulated, to evaluate the potential hazard. An instrument capable of providing the critical data required in such a study must have several features not usually found in instruments now available. First of all, the instrument must have a reaction vessel and associated components which closely simulate the structure and operation of a typical chemical plant reactor, such as a Pfaudler reactor. Secondly, the reaction mixture must be continuously stirred to simulate the actual conditions which occur in a plant reactor. A third consideration is that the reaction must be conducted in a truly adiabatic environment to simulate the worst possible condition, i.e. a runaway reaction. To do this, a means must be provided for compensating out the heat capacity contribution of the reactor. The apparatus of this invention answers this need by providing an instrument which incorporates the features set out above.

SUMMARY OF THE INVENTION

The invention concerns an adiabatic calorimeter apparatus, and method of use, for measuring the energy change in a chemical reaction. In this system the reaction vessel closely simulates a typical reactor used in chemical process work. The heat capacity of the reaction vessel is compensated out by electrical energy to achieve a highly accurate measurement of the temperature change which takes place in an exothermic reaction. In this apparatus the reaction vessel is suspended in an oven chamber having a gas atmosphere which surrounds the reaction vessel.

A jacket cover is fitted over the reaction vessel, such that the cover is in contact with the outer wall surface of the reaction vessel. A heater means and temperature measuring means are positioned inside the reaction vessel. A second heater means is secured to the outside of the jacket cover. The temperature measuring means is electrically connected into a temperature recorder unit.

A first stage temperature control unit is positioned outside the oven chamber. This temperature control is electrically connected into the heater means on the jacket cover, and into a temperature sensor inside the reaction vessel, and an opposing temperature sensor attached to the outside of the jacket cover. A stirring means inside the reaction vessel continuously stirs the reactants during the exothermic reaction.

The apparatus also includes a second stage temperature control. This control system includes a temperature control unit which is electrically connected into a heater inside the oven chamber, and into one temperature sensor attached to the outside of the jacket cover and an opposing temperature sensor attached to an inner wall surface of the oven chamber.

DESCRIPTION OF THE DRAWING

The single FIGURE shown herein is a drawing, partly in section, and in schematic illustration, of one embodiment of the adiabatic calorimeter apparatus of this invention.

DESCRIPTION OF A PREFERRED EMBODIMENT

In the drawing the numeral 10 generally indicates an adiabatic calorimeter apparatus. Apparatus 10 includes an oven chamber 11 which has a gas atmosphere therein. A reaction vessel 12 is fitted inside of a jacket cover 13 and this assembly is suspended inside the oven chamber by small diameter wires or cords 14. Wires 14 are fabricated of materials which have low thermal conductivity. The reaction vessel is suspended at the approximate geometric center of the oven chamber to achieve good thermal isolation. One end of each wire 14 is fastened to an eye bolt 15, which is secured to a metal ring 16 secured to the outside of jacket 13.

The outer surface of the oven chamber is covered with a layer 11a of high temperature insulation material which helps to reduce heat loss, by convection, from the oven. A resistance heater wire 17, of a copper nickel composition (Constantan) is wound around the outside of cover 13. The heater wire 17 fits into grooves (not shown) which are machined into the outer surface of the cover. At the bottom of reaction vessel 12 the jacket cover 13 does not completely cover the vessel, so that there is a small opening 18 in the cover. A lid 19 is secured to the top of the reaction vessel 12. The outer edge of lid 19 defines a beveled surface with a groove 20 therein. An O-ring 21 fits into groove 20.

When lid 19 is in position on the body of vessel 12 the beveled surface of the lid fits against a similar beveled surface on the vessel body. The O-ring thus makes a tight seal between the lid and the vessel. A screw cap 22 engages a corresponding threaded portion at the outer edge of the top of reaction vessel 12. Several cap screws 23, which are threaded into cap 22, bear against the upper surface of lid 19. The cap screws thus force the lid down against the beveled surface on the body of vessel 12.

Means for heating the reactants in vessel 12 is provided by a heater element 24, which fits inside a heater well 25. In practice, a bifilar wound resistance element is used. The upper end of the heater well, which is open, extends through lid 19 and is sealed to the lid. The lower end of well 25 extends down into vessel 12 to a point just above the bottom of the vessel. Well 25 is closed at the lower end to prevent chemical reactants from entering the well.

Heater element 24 is connected by electrical leads 26 and 27 into a constant current power supply 28. The temperature of the reaction taking place in vessel 12 is continuously measured by a thermometer 29, which fits inside of a thermometer well 30. A sensitive resistance thermometer or electronic digital thermometer may be used. In practice, a digital thermometer is preferred. The thermometer well 30, like the heater well 25, has an open upper end which extends through lid 19 and is sealed to the lid. Also, the lower end of well 30 is closed and the closed end extends down into vessel 12 to a point just above the bottom of the vessel.

The dimensions of heater well 25 and thermometer well 30 are such that heater element 24 and thermometer 29 can be interchanged, to fit in either well. Thermometer 29 is connected by electrical leads 31 and 32 into a temperature recorder unit 33. The calorimeter apparatus 10 has a first stage and second stage temperature control to insure that the chemical reaction takes place in an adiabatic environment. The primary function of the first stage temperature control is to utilize electrical energy to compensate out the heat capacity value of the reaction vessel 12. The first stage temperature control includes a temperature control unit 34, which connects into an AC power supply. The preferred component is a commercially available, three-action, computing-type controller.

The temperature of the reactive mix 35 is sensed by a thermocouple 36, which is located inside the reaction vessel 12. The preferred component is a single element thermocouple, comprising a nickel-chromium (Chromel-P) and copper-nickel (Constantan) alloy composition. An electrical lead 37 connects thermocouple 36 into temperature control unit 34. Thermocouple 36 is opposed by a similar thermocouple 38, which is attached to the outer wall surface of reaction vessel 12. An electrical lead 39 connects thermocouple 36 into thermocouple 38. A second electrical lead 40 connects thermocouple 38 into the temperature control unit 34.

The temperature control unit 34 is also connected into the heater wire 17 by an electrical lead 41. The second stage temperature control has the primary function of preventing heat loss from the reaction vessel into the gas environment in oven chamber 11. The second stage temperature control includes a temperature control unit 42, which connects into an AC power supply. Control 42 is a three-action controller of the same type as temperature control unit 34. Means for heating the gas atmosphere in oven chamber 11 is provided by one or more resistance heaters. In the drawing only one heater 43 is shown. Heater 43 is connected into temperature control unit 42 by electrical leads 44 and 45.

The second stage temperature control also includes four thermocouple sensors attached to jacket cover 13, which are opposed by four similar thermocouples attached to the inner wall of oven chamber 11. The thermocouple sensors on the jacket cover are indicated by numeral 46 and those on the oven wall by numeral 47. These thermocouple sensors are commercially available compositions having a nickel-chromium (Chromel-P) and copper-nickel (Constantan) composition. Thermocouple 46 is connected into temperature control unit 42 by an electrical lead 48. A second electrical lead 49 connects thermocouple 47 into the temperature control unit. Another electrical lead 50 connects the two thermocouple together.

In the practice of this invention the second stage temperature control is not critical to maintaining an adiabatic environment around the reaction vessel. If the second stage control should malfunction, any heat loss from the reactive mix into the gas atmosphere in the oven chamber would be overcome by extra heat supplied to jacket cover 13 by temperature control unit 34.

During a reaction the reaction mixture 35 is continuously stirred by a resin-coated metal stir bar 51, which sits on the bottom of the reaction vessel 12. The stir bar 51 is rotated by a magnet 52, mounted at the upper end of a rotatable shaft 53. The shaft is driven by a motor (not shown) which is positioned below the oven chamber 11. In addition to stirring the reaction mixture, the gas atmosphere in oven chamber 11 is continuously circulated, in a symmetrical pattern, around the reaction vessel 12 and jacket cover 13. The purpose of circulating the gas atmosphere, usually air, is to minimize heat transfer, either toward or away from the reaction vessel.

The gas circulating means is provided by a fan blade 54, which is mounted on shaft 53 and is enclosed by a circular skirt 55. The combination of the fan and skirt creates a venturi effect which causes the atmosphere to circulate in a symmetrical pattern around the reaction vessel and jacket cover. In some thermal hazard studies it may be desirable to measure the pressure generated during the chemical reaction, as well as the temperature change. In the present apparatus the pressure measurement is obtained by a pressure transducer 56, which is mounted on lid 19 of reaction vessel 12. The transducer is connected to a pressure recorder 57 by electrical leads 58 and 59. In practice, the pressure readings are transmitted by transducer 56, in the form of electrical signals, to recorder 57, which gives the readout in pressure units.

The calorimeter apparatus 10 also includes a pressure relief system, to insure adequate protection for the reaction vessel 12 in the event of an over pressure condition. This system is provided by a frangible disc 58, fabricated of nickel metal, and set to rupture at a pressure value substantially below the pressure rating of vessel 12. The disc 58 is placed in the bore of a conventional pressure fitting 59 and is backed up by a nickel washer (not shown). A small diameter conduit 60 connects the fitting 59 with a blow-down tank (not shown). If an over pressure condition occurs in vessel 12, disc 58 will rupture and allow part of the contents in vessel 12 to discharge into the blow-down tank through conduit 60.

The calorimeter apparatus 10 is further provided with a system which allows the operator to separate the chemical reactants prior to reaction. For example, in certain polymerization reactions a catalyst may be used to initiate the reaction, or to accelerate the reaction. In this situation the catalyst is kept separated from the other reactants until it is desired to commence the reaction. This system includes a small diameter tube section 61, for containing the reactants to be added to vessel 12. A conduit 62 connects the upper end of tube 61 into a source of gas under pressure, such as nitrogen. The bottom end of tube 61 is connected into the reaction vessel 12 by a conduit 63 and fitting 64.

Valves 65 and 66 control the flow of gas into and out of tube section 61. In a typical operation the chemical reactants are charged to the reaction vessel 12. The vessel 12 is then purged with the nitrogen gas, or by releasing vapors which have accumulated in the vessel. Following the purge step the catalyst is loaded into tube 61 and the valves 65 and 66 are both opened. This allows the pressurized gas to force the catalyst into the reaction vessel.

The following example is given to illustrate the practice of this invention:

EXAMPLE

The objective in this example was to determine the adiabatic temperature rise, due to the heat of polymerization, which occurs in the polymerization of a vinylidene chloride monomer to form polyvinylchloride. In addition to measuring temperature change, pressure measurements were taken to determine the total pressure generated during the polymerization reaction. Both the temperature and pressure values were obtained as a function of time.

The starting material was vinylidene chloride monomer in water. The composition consisted of 98.73 grams vinylidene chloride monomer, 150.07 grams water, and 0.59 gram of an organic peroxide. The 249.4 gram mixture was weighed into the reaction vessel at room temperature. The reaction vessel was placed in the jacket cover 13 and purged with nitrogen to remove air trapped in the vessel. Heater element 24 and thermometer 29 were set in their respective well members. The heater was connected into power supply 28 and the thermometer into temperature recorder 33. The reaction vessel was closed and pressure transducer 56 was attached to the vessel and connected into the pressure recorder 57. The thermocouple sensors 36 and 38 were also installed in operating position and connected into temperature control unit 34.

The temperature control units 34 and 42 were both turned on to bring the temperature of the system up to equilibrium. At the same time, the stir bar 51 was set in motion by turning on the motor which drives shaft 53 and magnet 52. The constant current power supply 28 was turned on to begin slowly heating the sample mixture 35 in the reaction vessel. During the heating sequence the temperature rise was continuously monitored by a thermometer 29 and recorded as digital values on a computer printout associated with recorder 33. At the same time, the pressure measurement readings were monitored by transducer 56 and transmitted by recorder 57 to the computer printout.

When the temperature of the sample mix had risen to 46.6° C., the polymerization reaction had commenced. This was indicated by the upward slope of a plot line on a strip chart in recorder 33. At this point the exothermic reaction became self-heating and the power supply 28 was turned off. After a period of 200 minutes from beginning of the exotherm, the plot line changed from an upward slope to a linear trace, indicating completion of the reaction. The temperature reading at this point was 140.13° C., indicating a total temperature rise of 93.5° C. During the course of the reaction the vapor pressure reading went from about 30 p.s.i.a. to about 210 p.s.i.a.

After the reaction was complete both of the temperature control units were shut off and the stir bar was stopped. The reaction vessel was removed from the jacket cover and allowed to cool to room temperature. After cooling, a sample of the gas phase in the reaction vessel was collected and analyzed in a mass spectrometer. The gas analysis was conducted to determine the extent of decomposition of the reaction product, and to determine whether any side reactions had taken place.

The adiabatic temperature rise data obtained in the experiment described in the example was compared with data calculated from known values relating to heat of polymerization of vinylidene chloride. The comparison indicates that the present calorimeter apparatus is capable of providing temperature data which is within 10 percent of theory.

The data used for calculating the heat of polymerization of vinylidene chloride is given by H. A. Skinner in "Experimental Thermochemistry", Vol. II, Interscience Publishing Co. (1962), as follows:

The heat capacities (Cp) are given as 0.3 cal./(g.) (deg.C.) for vinylidene chloride, 0.98 cal./(g.) (deg. C.) for water, and 0.5 cal./(g.) (deg. C.) for the organic peroxide.

The heat of polymerization ($\Delta H_p$) of vinylidene chloride is given as $-18.0 \pm 0.7$ kcal./g-mole.

From these figures the sum of the heat capacities ($\Sigma C_p$) for the reactants is calculated as:

98.73 g. × 0.3 cal./(g.) (deg. C.) = 29.6 cal./deg C.

150.07 g. × 0.98 cal./(g.) (deg. C.) = 147.07 cal./deg. C.

0.59 g. × 0.5 cal./(g.) (deg. C) = 0.3 cal./deg. C., which gives $\Sigma C_p$ = 177.0 cal./deg. C.

The amount of heat expected from the polymerization reaction is calculated as follows:

98.73 = grams of vinylidene chloride monomer
96.94 = gram molecular weight of vinylidene chloride
$\frac{98.73}{96.94}$ = 1.0185 moles of monomer reacted 1.0185 moles × −18,000 cal./mole = −18,330 calories = heat of polymerization. (Negative sign indicates exothermic reaction).

The adiabatic temperature rise can then be determined from the equation:

$$\Delta T_A = \frac{Q}{\Sigma C p}$$

where
$\Delta T_A$ = adiabatic temperature rise (in deg. C.)
Q = heat of reaction (in calories)
$\Sigma C_p$ = heat capacity (in cal./deg. C.)

Substituting the figures obtained in the calculations above:

$$\Delta T_A = \frac{18,330}{177} = 103.6 \text{ deg. C.}$$

Referring to the example, the adiabatic temperature rise during the polymerization reaction, as measured by the calorimeter apparatus, was 93.5°. Comparing this with the calculated figure of 103.6°, brings the measured value within 10 percent of theory. In the example described above the measured value (93.5 deg.) was not corrected for a temperature depression which occured when a small amount of water was vaporized in the closed reaction vessel when the temperature had exceeded 100° C. This correction would tend to make the measured value agree more closely with the calculated value.

In a chemical hazard study, such as polymerization of vinylidene chloride, there may be a need for various data which can be derived from the time/temperature data obtained in such a study. For example, the following types of data can be useful to chemical engineers in designing reactors, storage vessels, piping systems, control instrumentation, and the like:

A. The rate of adiabatic temperature rise in a runaway reaction, which means:
the temperature rate as a function of time, and
the temperature rate as a function of temperature.

B. The rate of pressure rise in a runaway reaction, which means:
the pressure rate as a function of time, and
the pressure rate as a function of temperature.

C. The vapor pressure of the reaction mixture in a runaway reaction, which means:
the pressure exerted by the vapor phase of the reaction mixture at any given temperature during the reaction.

In the practice of this invention each bit of data described above can be taken simultaneously, as the reaction proceeds, and recorded in the form of a digital print-out by a computer system associated with the calorimeter apparatus. In some chemical hazard studies there may be a need to obtain (1) only temperature data (i.e. temperature/time), or (2) only pressure data (i.e. pressure/time). The calorimeter apparatus of this invention can be used in either situation to provide the required information. In actual practice the present calorimeter apparatus can also be utilized to conduct a heat of reaction study.

Other details, such as materials of construction, general operating conditions, and novel features of the calorimeter apparatus will now be discussed. These details are for the purpose of further describing the structure and operation of this apparatus, but are not intended as a limitation on the practice of the invention. The reaction vessel 12 may be constructed of various steel alloys, such as stainless steel; non-ferrous metals, such as aluminum, copper, magnesium, titanium, and tantalum. Other materials include glass-coated steel, or steel coated with a refractory material, such as Alundum ® fused-alumina refractory compositions. The jacket cover 13 is preferably constructed of a light metal, such as aluminum.

The first and second stage temperature control systems provide a distinct advantage over the prior calorimeter instruments used in chemical hazard research. In the operation of the first stage temperature control any temperature difference between the reactive mix 35 and the jacket cover 13 is sensed by thermocouples 36 and 38. When this occurs a differential voltage signal is sent to the temperature control unit 34. In response to this signal the three-action controller modulates heat into the jacket cover to maintain the temperature of the reaction vessel at the same level as the reactive mix. The first stage temperature control thus removes the heat capacity effect of the reaction vessel and permits a precise measurement of the adiabatic temperature rise which takes place in the vessel.

The second stage temperature control provides an additional system for insuring an adiabatic environment in which the reaction can proceed. In the operation of this control loop the thermocouple groups 46 and 47 will sense any temperature difference between the reaction vessel and the jacket cover and the environment in the oven chamber 11. When a temperature difference occurs a corresponding signal to the control unit 42 causes it to step up power to heater 43 and bring the environment temperature up to that of the reaction vessel. The present calorimeter apparatus is capable of temperature measurements over a range of from about −40° C. to 1000° C. and pressure measurements up to about 4000 p.s.i.

The invention claimed is:

1. An adiabatic calorimeter apparatus for measuring the energy change in a chemical reaction, the apparatus comprising:
an oven chamber;
a reaction vessel which is positioned in the oven chamber and is adapted to contain one or more chemical reactants;
the oven chamber containing a gas atmosphere which surrounds the reaction vessel;
a jacket cover which is fitted to the reaction vessel and is in contact with the outer wall surface of the reaction vessel;
a temperature measuring means positioned in the reaction vessel;
a temperature recorder unit which is electrically connected into the temperature measuring means;
a first heater means which is positioned in the reaction vessel;
a second heater means which is attached to an outer wall surface of the jacket cover;
a first temperature control system which includes a first temperature sensor positioned in the reaction vessel, a second temperature sensor attached to the outer wall surface of the reaction vessel, the second heater means, and a first temperature control unit positioned outside of the oven chamber and electrically connected to the first and second temperature sensors and the second heater means;
the first temperature control unit thereby controlling power input to the second heater means on the jacket cover, such that the temperature of the reaction vessel is maintained in equilibrium with the temperature of the chemical reactants contained in the reaction vessel; and
a stirring means positioned in the reaction vessel and operatively associated with a means for actuating the stirring means.

2. The apparatus of claim 1 which further includes a second temperature control system, the control system including a third temperature sensor attached to the outer wall surface of the jacket cover, a fourth temperature sensor attached to an inner wall surface of the oven chamber, a third heater means positioned inside the oven chamber, and a second temperature control unit positioned outside of the oven chamber, and electrically connected to the third and fourth temperature sensors and the third heater means.

3. The apparatus of claim 1 which further includes a pressure measuring means, the pressure measuring means being attached to the reaction vessel and connected into a pressure recorder unit.

4. The apparatus of claim 1 which further includes a transfer vessel, the transfer vessel being in communication with the reaction vessel and in communication with a gas source.

5. The apparatus of claim 1 which further includes a means for circulating the gas atmosphere in the oven chamber, said circulating means being positioned in the oven chamber.

6. The apparatus of claim 5 in which the circulating means is defined by a fan blade mounted on a rotatable shaft and enclosed by an open end duct member.

7. The apparatus of claim 1 in which the oven chamber is a box-shaped chamber, and the reaction vessel is suspended in the geometric center of the oven chamber by suspension means attached to the reaction chamber and to an inner wall surface of the reaction chamber.

8. The apparatus of claim 1 in which the stirring means is a metal stir bar and the actuating means is a magnet mounted on a rotatable shaft, the magnet being positioned in the oven chamber below the reaction vessel.

9. The apparatus of claim 1 which further includes a pressure relief system defined by a frangible disc installed in a conduit which connects the reaction vessel into a blow-down tank.

10. The apparatus of claim 1 in which the first heater means is a resistance wire heater installed in a well member, and the well member is positioned inside the reaction vessel.

11. The apparatus of claim 1 in which the second heater means is a resistance wire which is installed on the outer surface of the jacket cover.

12. The apparatus of claim 1 in which the temperature measuring means is a resistance thermometer installed in a well member, and the well member is positioned inside the reaction vessel.

13. The apparatus of claim 1 in which the first and second temperature sensors are thermocouples.

14. A method for measuring the energy of a chemical reaction in an adiabatic calorimeter apparatus, the apparatus including a reaction vessel fitted with a jacket cover, the vessel and jacket cover being suspended in an oven chamber and surrounded by a gas atmosphere contained in the oven chamber, the jacket cover having a heater means attached thereto, and the heater means being operably associated with a temperature control unit, the method comprising the steps of:

placing one or more chemical reactants in the reaction vessel;

heating the chemical reactants to a temperature which will initiate the exothermic reaction of the reactants;

continuously stirring the chemical reactants, while allowing the exothermic reaction to proceed to completion;

controlling power input to the heater means on the jacket cover to thereby maintain the temperature of the reaction vessel in equilibrium with the temperature of the chemical reactants in the reaction vessel;

continuously measuring and recording the temperature of the chemical reactants during the exothermic reaction to measure the temperature change which occurs between the beginning of the exothermic reaction and completion of said reaction; and recording the time required for the entire temperature change to take place.

15. The method of claim 14 which further includes the step of measuring and recording the amount of pressure generated by the chemical reaction taking place in the reaction vessel.

16. The method of claim 14 which includes the step of continuously circulating the gas in the reaction chamber in a symmetrical pattern.

* * * * *